United States Patent [19]

Gory et al.

[11] Patent Number: 5,387,189
[45] Date of Patent: Feb. 7, 1995

[54] ELECTROTRANSPORT DELIVERY DEVICE AND METHOD OF MAKING SAME

[75] Inventors: J. Richard Gory, San Jose; John R. Peery, Stanford, both of Calif.

[73] Assignee: ALZA Corporation, Palo Alto, Calif.

[21] Appl. No.: 161,371

[22] Filed: Dec. 2, 1993

[51] Int. Cl.[6] .................................................. A61N 1/30
[52] U.S. Cl. .................................................. 604/20; 607/152
[58] Field of Search ............... 604/20; 607/149, 151, 607/152

[56] References Cited

U.S. PATENT DOCUMENTS

| | | | |
|---|---|---|---|
| 4,474,570 | 10/1984 | Ariura et al. | 604/20 |
| 4,883,457 | 11/1989 | Sibalis | 604/20 |
| 4,968,297 | 11/1990 | Jacobsen et al. | 604/20 |
| 4,973,303 | 11/1990 | Johnson et al. | 604/20 |
| 4,979,938 | 12/1990 | Stephen et al. | 604/20 |
| 5,006,108 | 4/1991 | LaPrade | 604/20 |
| 5,032,110 | 7/1991 | Watanabe | 604/20 |
| 5,037,380 | 8/1991 | Jacobsen et al. | 604/20 |
| 5,047,007 | 9/1991 | McNichols | 604/20 |
| 5,087,241 | 2/1992 | Mathiesen et al. | 604/20 |
| 5,087,242 | 2/1992 | Petelenz et al. | 604/20 |
| 5,088,978 | 2/1992 | Hillman et al. | 604/20 |
| 5,135,479 | 8/1992 | Sibalis et al. | 604/20 |
| 5,135,480 | 8/1992 | Bannon et al. | 604/20 |
| 5,158,537 | 12/1992 | Haak et al. | 604/20 |
| 5,167,617 | 12/1992 | Sibalis | 604/20 |
| 5,169,383 | 12/1992 | Gyory et al. | 604/20 |
| 5,203,768 | 4/1993 | Haak et al. | 604/20 |
| 5,224,927 | 7/1993 | Tapper | 604/20 |
| 5,236,412 | 8/1993 | Lloyd et al. | 604/20 |
| 5,322,502 | 6/1994 | Theeuwes et al. | 604/20 |
| 5,328,453 | 7/1994 | Sibalis | 604/20 |
| 5,328,454 | 7/1994 | Sibalis | 604/20 |

FOREIGN PATENT DOCUMENTS

3020789A1  1/1982  Germany .

*Primary Examiner*—John D. Yasko
*Attorney, Agent, or Firm*—D. Byron Miller; Steven F. Stone; Edward L. Mandell

[57] ABSTRACT

An apparatus for supplying power to deliver a beneficial agent or drug though a body surface of a patient is provided. In a first embodiment, the invention includes a power supply (eg, a battery 118, 119) and optionally other electrical components (126, 128), positioned in a pocket (114) formed in a supporting substrate (112). Electrically conducting traces (113, 116) positioned on the substrate (112, 113) form an electrical power network connecting the battery (118, 119) to the other electrical components (126, 128), for control and delivery of electrical power. The traces may be electrically conducting adhesive strips (206). In a second embodiment, a waterproof enclosure provides moisture isolation of electrical components in an electrical power network. The waterproof enclosure may be selectively formed around one or a group of electrical components (202, 204, 218) by sealing a sealant film (208, 210). External outputs (207,209) are provided to make electrical contact with closely adjacent electrodes (D, C) at least one of which holds a liquid containing a therapeutic agent.

21 Claims, 3 Drawing Sheets

ELECTROTRANSPORT DELIVERY DEVICE AND METHOD OF MAKING SAME

TECHNICAL FIELD

This invention relates to electrotransport drug delivery, and more particularly to power sources and electronic circuits for controlling and driving electrotransport drug delivery systems.

BACKGROUND ART

The term "electrotransport" as used herein refers generally to the delivery of an agent (eg, a drug) through a membrane, such as skin, mucous membrane, or nails, which delivery is induced by application of an electrical potential. For example, a beneficial therapeutic agent may be introduced into the systemic circulation of a human body by electrotransport delivery through the skin. A widely used electrotransport process, iontophoresis, involves the electrically induced transport of charged ions. Another type of electrotransport, electroosmosis, involves the flow of a liquid, which liquid contains the agent to be delivered, under the influence of an electric field. Still another type of electrotransport process, electroporation, involves the formation of transiently-existing pores in a biological membrane by the application of an electric field, through which pores an agent can be delivered either passively (ie, without electrical assistance) or actively (ie, under the influence of an electric potential). However, in any given electrotransport process, more than one of these processes may be occurring simultaneously to a certain extent.

Accordingly, the term "electrotransport", as used herein, should be given its broadest possible interpretation so that it includes the electrically induced or enhanced transport of at least one agent, which may be charged, uncharged, or a mixture thereof. regardless of the specific mechanism or mechanisms by which the agent actually is transported.

Electrotransport devices generally use at least two electrodes which are in electrical contact with some portion of the skin, nails, mucous membrane, or other surface of the body. One electrode, commonly referred to as the "donor" or "active" electrode, is the electrode from which the agent is delivered into the body. The other electrode, typically termed the "counter" or "return" electrode, serves to close the electrical circuit through the body. For example, if the agent to be delivered is positively charged, ie, a cation, then the anode is the active or donor electrode, while the cathode serves to complete the circuit. Alternatively, if an agent is negatively charged, ie, an anion, the cathode is the donor electrode. Additionally, both the anode and cathode may be considered donor electrodes, for example, if both anionic and cationic agent ions are to be delivered from the cathode and anode, respectively.

Furthermore, electrotransport delivery systems generally require at least one reservoir or source of the agent to be delivered to the body. Examples of such donor reservoirs include a pouch or cavity, a porous sponge or pad, and a hydrophilic polymer or a gel matrix. Such donor reservoirs are electrically connected to, and positioned between, the anode or cathode and the body surface, to provide a fixed or renewable source of one or more agents or drugs. Electrotransport devices also have an electrical power source such as one or more batteries. Typically, one pole of the power source is electrically connected to the donor electrode, while the opposite pole is electrically connected to the counter electrode. In addition, some electrotransport devices have an electrical controller which controls the current applied through the electrodes, thereby regulating the rate of agent delivery. Furthermore, passive flux control membranes, adhesives for maintaining device contact with a body surface, insulating members, and impermeable backing members are some other potential components of electrotransport devices.

As used herein, the terms "agent" and "drug" are used interchangeably and are intended to have broad application and to refer to any therapeutically active substance that is delivered to a living organism to produce a desired, usually beneficial, effect. In general, this includes therapeutic agents in all of the major therapeutic areas including, but not limited to: anti-infectives such as antibiotic and antiviral agents; analgesics, and analgesic combinations; anesthetics, anorexics; antiarthritics; antiasthmatic agents; anticonvulsants; antidepressants; antidiabetic agents; antidiarrheals; antihistamines; anti-inflammatory agents; antimigraine preparations; antimotion sickness preparations; antinauseants; antineoplastics; antiparkinson drugs; cardiostimulants; antipruritics; antipsychotics; antipyretics; antispasmodics, including gastrointestinal and urinary; anticholinergics; sympathomimetrics; xanthine derivatives; cardiovascular preparations, including calcium blockers; beta blockers; beta-agonists; antiarrythmics; antihypertensives; ACE inhibitors; diuretics; vasodilators, including general, coronary, peripheral and cerebral; central nervous system stimulants; cough and cold preparations; decongestants; diagnostics; hormones; hypnotics: immunosuppressives; muscle relaxants; parasympatholytics; parasympathomimetrics; prostaglandins; proteins; peptides; psychostimulants; sedatives and tranquilizers.

All electrotransport agent delivery devices utilize an electrical "power network" to electrically connect the power source (eg, a battery) to the electrodes. In very simple devices, such as those disclosed by Ariura et al in U.S. Pat. No. 4,474,570, the power network is merely the battery and a conductive wire used to connect the battery to an electrode. Other devices use a variety of electrical components to control the amplitude, polarity, timing, waveform shape, etc. of the electric current supplied by the power source. See, for example, U.S. Pat. No. 5,047,007, issued to McNichols et al.

Commercial transdermal electrotransport drug delivery devices (eg, the Phoresor, sold by Iomed, Inc. of Salt Lake City, Ut.; the Dupel Iontophoresis System sold by Empi, Inc. of St. Paul, Mn.; the Webster Sweat Inducer, sold by Wescor, Inc. of Logan, Ut) generally utilize a desk-top electrical power supply unit and a pair of skin contacting electrodes. The donor electrode contains a drug solution while the counter electrode contains a solution of a biocompatible electrolyte salt. Examples of "satelite" electrode assemblies which are adapted for use with a desk-top electrical power supply unit are disclosed in Lloyd et al U.S. Pat. 5,236,412; Hillman et al U.S. Pat. No. 5,088,978; Patelenz et al U.S. Pat. No. 5,087,242; Mathiesen et al 5,087,241; Jacobsen et al U.S. Pat. No. 5,037,380; LaPrade U.S. Pat. No. 5,006,108; Stephen et al U.S. Pat. No. 4,979,938; Johnson et al U.S. Pat. No. 4,973,303; Jacobsen et al U.S. Pat. No. 4,968,297; and elsewhere. The satelite electrodes are connected to the electrical power supply unit by long (e.g., 1–2 meters) electrically conductive wires. In this type of design configuration, there is no danger of the liquid drug/salt solutions contaminating the electrical circuitry in the desk-top power supply unit since they are far removed from one another. In general, the satelite electrodes are comprised of a receptacle or a matrix for holding the drug/salt solution, a current distributing member and a means for connecting the current distributing member to the long electrically conductive wire/cable. In general, the satelite electrodes contain no electrical components for generating or controlling the electric current applied by the device.

More recently, small self-contained electrotransport delivery devices adapted to be worn on the skin, sometimes unobtrusively under clothing, for extended periods of time have been proposed. The electrical power networks in such miniaturized electrotransport drug delivery devices are also preferably miniaturized, and may be in the form of either integrated circuits (i.e., microchips) or small printed flexible circuits. Conventional printed circuits are formed by printing or otherwise depositing electrically conductive pathways on a flexible substrate, usually in the form of a polymer sheet. Electronic components, such as batteries, resistors, pulse generators, capacitors, etc., are electrically connected to form an electrical power network which generates and/or controls the amplitude, polarity, timing, waveform shape, etc. of the electric current which is the driving force for the delivery of the drug or other beneficial agent. Such small self-contained electrotransport delivery devices are disclosed for example in Tapper U.S. Pat. No. 5,224,927; Haak et al U.S. Pat. No. 5,203,768; Gyory et al U.S. Pat. No. 5,169,383; Watanabe U.S. Pat. No. 5,032,110; Sibalis U.S. Pat. No. 5,167,617; Bannon et al U.S. Pat. No. 5,135,480; Sibalis et al U.S. Pat. No. 5,135,479; Sibalis U.S. Pat. No. 4,883,457 and Ariura et al U.S. Pat. No. 4,474,570. One design problem which is inherent in any small wearable electrotransport device is that the electrical network which powers the device and controls the level of applied current must be adequately protected from contamination from external liquids such as water from bathing. The prior art recognized this and water-proof backings have been used to prevent contamination from external liquids. See Haak et al U.S. Pat. No. 5,158,437. Sibalis U.S. Pat. No. 4,883,457 also teaches an adhesive seal surrounding an entire assembly of batteries and liquid containing electrodes in order to separate them from the external environment.

While the prior art has recognized the need to prevent the electrotransport drive/control power networks from being contaminated from contacting external liquids, there is still the potential problem of contamination from contacting the (usually aqueous) drug solution contained in the donor electrode reservoir and/or the salt solution contained in the counter electrode reservoir. What is needed is an electrotransport device, and a method of making same, which provides better insulation of the power supply and other electrical components from the wet (ie, liquid containing) portions of the device.

DISCLOSURE OF THE INVENTION

These needs are met by the invention, which provides methods and apparati for supply of power for an electrotransport device to deliver a beneficial drug or other agent through a body surface of a patient. An electrical network used to power an electrotransport delivery device is provided. The network comprises one or more electrical components and means for electrically connecting the components to a pair of power network outputs. At least one of the power network outputs is adapted for electrical connection to a closely adjacent electrode which holds a liquid containing the beneficial agent to be delivered. The network is positioned within a liquid-tight chamber. Each of the power network outputs are so positioned so that the outputs extend from inside the chamber to outside the chamber where they are accessible for electrical connection. The chamber is sealed in a liquid-tight manner to prevent the electrical components and the electrical connecting means from coming into contact with any liquid outside of the chamber.

MODES FOR CARRYING OUT THE INVENTION

Figure 1:
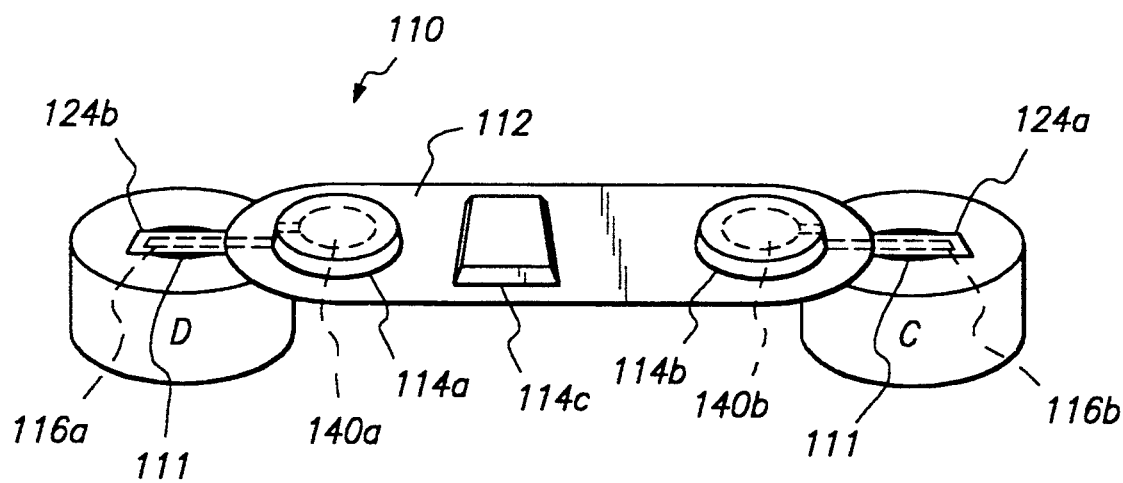
FIG. 1 is a perspective view of one embodiment of apparatus suitable for practicing the invention.

FIG. 1 is a perspective view of an electrotransport power supply network generally indicated as numeral 110 according to the present invention. The network 110 has a pair of outputs, in the form of electrically conductive circuit traces 116a, 116b which are electrically connected to closely adjacent liquid containing donor and counter donor electrodes. The electrodes are designated by D and C respectively. The electrical connection of the network outputs to the donor and counter donor electrodes is preferably made with an electrically conductive epoxy or other adhesive III.

Figure 2:
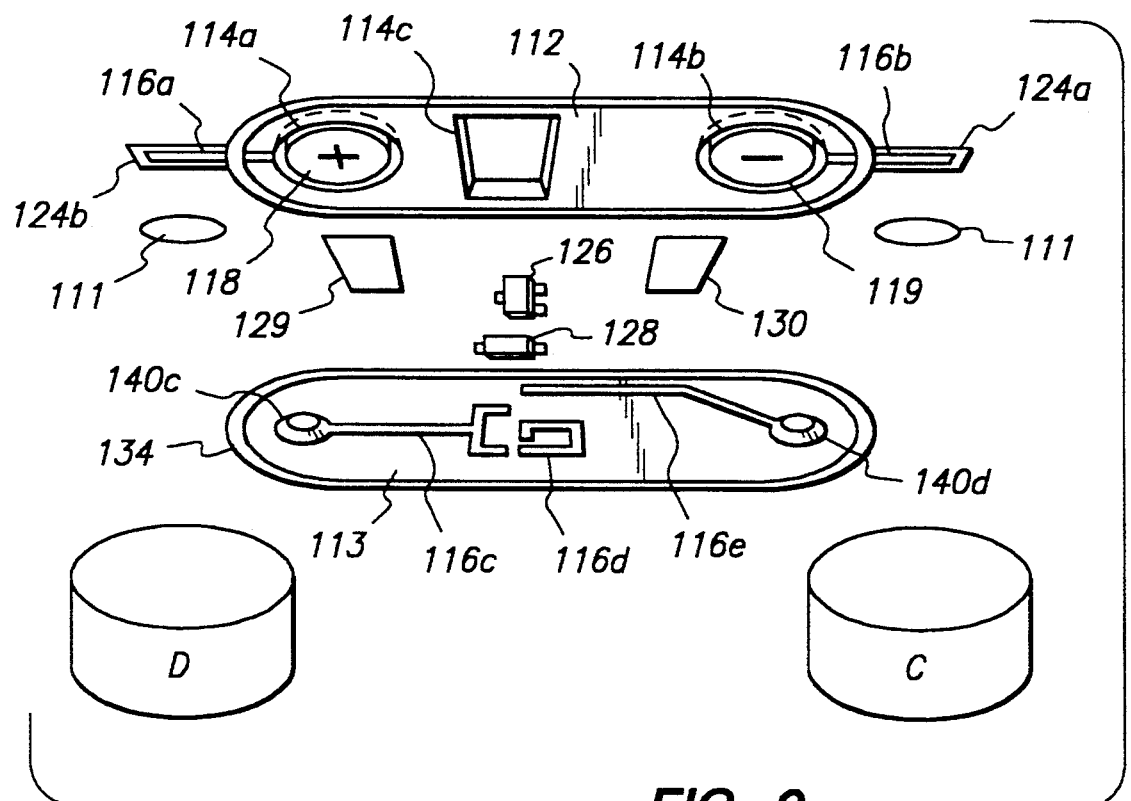
FIG. 2 is an exploded view of the apparatus illustrated in FIG. 1.

FIG. 2 is an exploded view of the power supply network 110. Vacuum-forming or thermo-forming techniques are used to create recessed pockets 114 in a top substrate 112. The top substrate 112 may, for example, be a polyester or polyamide layer of about 0.25 mm thickness or larger. The inside of top substrate 112 is coated with etched copper or silkscreened silver circuit traces 116a and 116b. Alternatively, the circuit traces 116a and 116b may be stamped from a metal sheet about 0.1–0.3 mm thick and positioned on the substrate 112 with a suitable adhesive. The top substrate 112 is extended laterally to form oppositely disposed support members 124a and 124b.

The pockets 114a and 114b hold batteries 118 and 119, respectively. The pocket 114c holds electrical components 126 and 128.

A bottom substrate 113 is adapted to be sealingly mated with top substrate 112, by sealing along the peripheral edges of substrates 112 and 113. The mated substrates 112 and 113 provide separate retaining chambers for the batteries 118, 119 and components 126 and 128. The inside of substrate 113 is similarly provided with conductive circuit traces 116c, 116d, and 116e to complete the interconnection of the power supply network 110.

The batteries 118 and 119 are aligned with embossed or raised conductive pads 140 on the circuit traces 116. The pads 140a and 140b on the inside of the substrate 112 are connected to the minus and plus terminals respectively of the batteries 118 and 119 and the circuit traces 116a and 116b by suitable means such as electrically conductive epoxy. The pads 140c and 140d on the inside of the substrate 113 connect the plus and minus terminals respectively of the batteries 118 and 119 to the circuit traces 116c and 116e. Thin, insulating shields 129 and 130 of suitable material such as polyester, polyurethane or other dielectric material are aligned and placed or printed such that they are between the circuit traces 116c and 116e and the batteries 118 and 119. These shields are provided to electrically isolate the circuit traces 116c and 116e from the adjacent minus and plus terminals of the batteries 118 and 119 and thus prevent inadvertent shorting of the batteries.

The assembly 110 is formed by sealing substrate 112 to substrate 113. The sealing may be accomplished either by heat sealing (if substrates 112 and 113 are made of a heat sealable material such as ethylene vinyl acetate copolymer, Elvax made by E.I. du Pont Denmours, Wilmington, De. or a thermoplastic elastomer such as Santoprene sold by Monsanto Co. of St. Louis, Mo. and Kraton sold by Shell Chemical Co. of Belpre, Oh.) or adhesively sealing substrates 112 and 113 together.

In the latter case, an electrically insulating, moisture impermeable adhesive layer 134 is aligned to, and holds the bottom substrate layer 112 to the top substrate layer 113. The layer 134 is interposed between, and in contact with, these two substrate layers. A suitable adhesive is Silicone Medical Adhesive, made by Dow Corning, Midland, Mi.

The assembly 110 is thereby provided with an electrically insulating, waterproof seal around the entire periphery of the substrate layers 112 and 113 including the portions of conductive traces 116a, 116b which pass through the sealed periphery.

Figure 3:
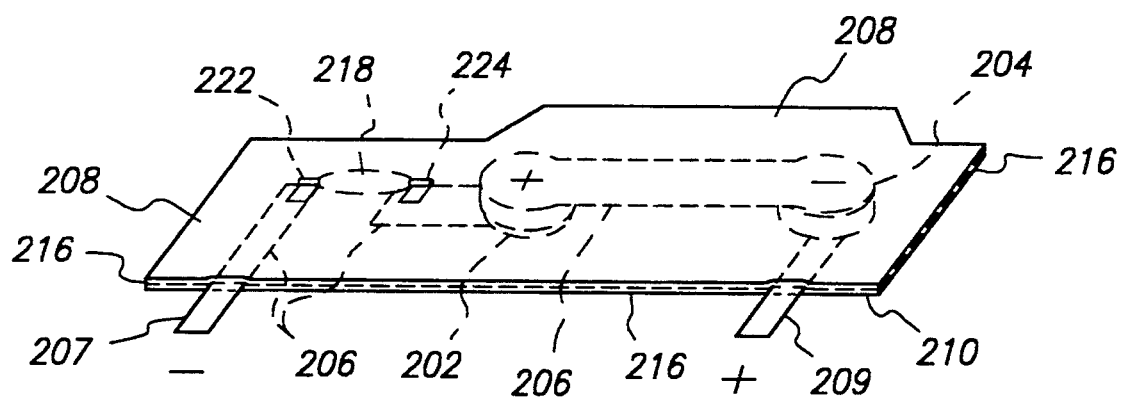
FIG. 3 is a perspective view of an alternate embodiment of a sealed electrical power network in accordance with the invention.
Figure 4:
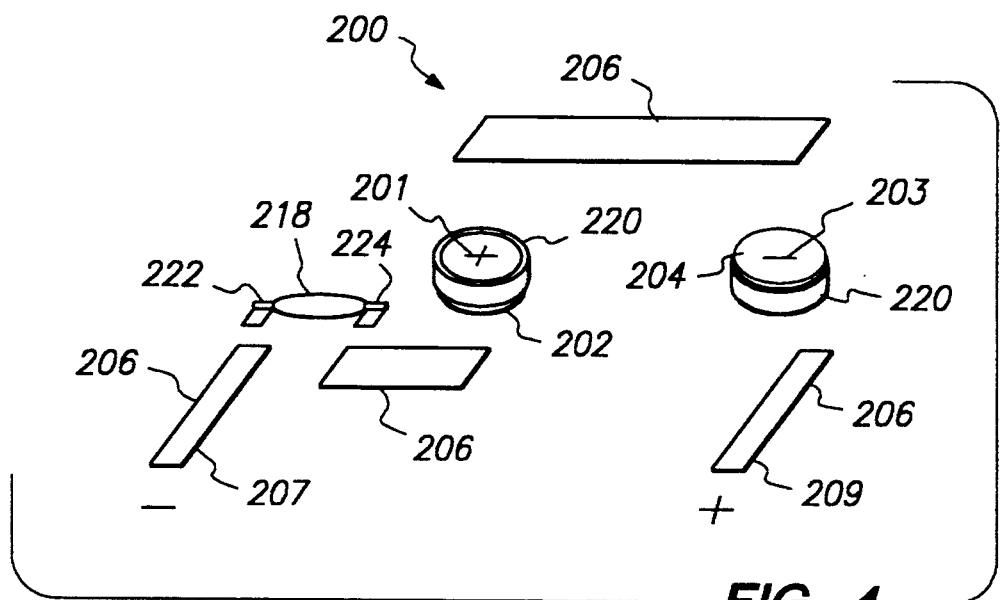
FIG. 4 is an exploded view of the power network illustrated in FIG. 3 with the sealing layers 208, 210 removed for ease of viewing.

With reference to FIGS. 3 and 4, another embodiment of an electrotransport power network is indicated generally by the numeral 200. The network 200 is constructed according to the present invention. Opposed terminals of batteries 202, 204 and leads 222, 224 of current controlling diode 218 are connected in series by individual strips of electrically conductive adhesive tape 206. Separate strips of conductive adhesive strips 206 extend outward from component 218 and battery 204 to form power network outputs 207 and 209 for connection to liquid-containing electrode assemblies (not shown).

The batteries 202 and 204 are each provided with an insulating rim 220 to electrically isolate the respective conductive strips 206 from shorting between the plus and minus terminals of the batteries where the strips 206 cross the outer diameter of the battery case. Button cell batteries of this type are available from Panasonic, Secaucus, N.J.

A suitable conductive adhesive strip for connecting the components of the power network 200 is an acrylate adhesive with conductive scrim coated with carbon particles or fibers such as ARCLAD 8001 made by Adhesives Research in Allentown, Pa.

A top layer 208 and a bottom layer 210, both layers composed of flexible, liquid-impermeable plastic film, is used to seal, enclose and mechanically support the batteries 202 and 204, component 218 and the conductive adhesive strips 206. At least the peripheral edges of layers 208 and 210 are sealed to one another in a liquid-tight manner to form a peripheral seal 216 which surrounds the power network 200.

One terminal 222 of component 218 contacts the adhesive, conductive surface of one conductive strip 206. This strip 206 extends beyond the enclosing layers 208 and 210, through the peripheral seal 216 to form a power network output 207. The positive terminal of battery 204 connects to another conductive strip 206 which extends beyond the sealed layers 208 and 210, through the peripheral seal 216 to form the second power network output 209.

In one embodiment a suitable material for the liquid-impenetrable film is a 0.03 to 0.05 mm polyurethane film coated with acrylate adhesive such as Flexcon XRU-100 made by Flexcon of Boston, Ma. In other embodiments, the layers 208 and 210 may be heat sealed, vacuum sealed or thermo-formed to make a liquid-tight and electrically insulating enclosure. Sealing the layers 208 and 210 completely around the peripheral area 216 forms a water-tight seal between the batteries 202 and 204, other electrical components 218, and the liquid containing electrodes (not shown in FIGS. 3 and 4) which are electrically connected to the power network outputs 207, 209. Preferably, the transverse width of the seal 216 is at least 3-7 mm.

Figure 5:
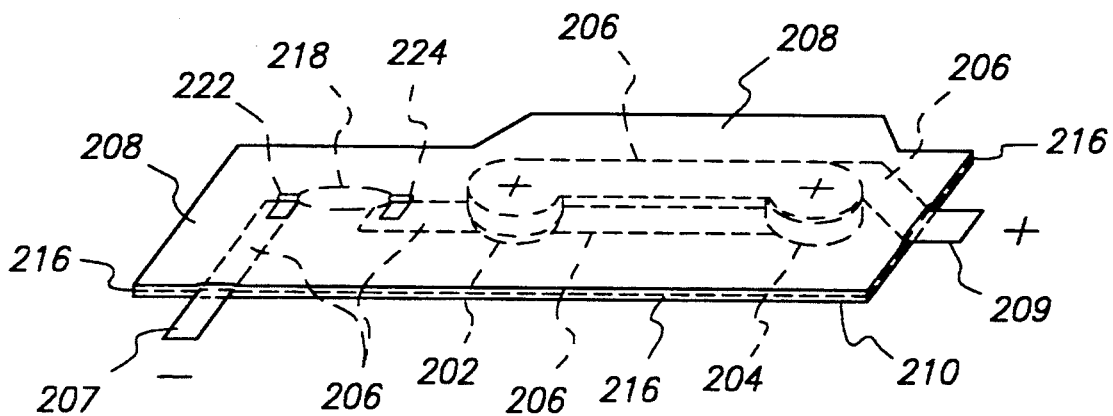
FIG. 5 is a perspective view of an embodiment in accordance with this invention using batteries in parallel.

In FIGS. 3 and 4, a strip of electrically conductive adhesive 206 provides electrical contact between the two uppermost terminals of the batteries 202 and 204, where the batteries are operated in series to provide higher voltage. Alternatively, first and second electrically conductive adhesive strips 206 can be placed in contact with the uppermost terminals and with the lowermost terminals, respectively, of the two batteries 202 and 204, if the two batteries are to be operated in parallel, as illustrated in FIG. 5.

This method of assembly avoids several process steps that would otherwise be used. The adhesive strips are also electrically conductive so that no additional materials need be provided for the circuit traces connected to the batteries 202 and 204. This approach also eliminates the hazards of using toxic materials for soldering on, and standard cleaning of, the assembly. Use of waterproof sealing sheets 208, 210 isolates the batteries 202, 204 from exposure not only to liquids (ie, bathing water) in the external environment but also to liquids contained in the "wet" portions of the donor and counter electrodes D and C (not shown in FIGS. 3 to 5). Thus, the power network 200 is sealed from coming into contact with the drug solution in the closely adjacent donor electrode D and the electrolyte salt solution in the closely adjacent counter electrode C.

A watertight seal may also be provided by coating one side of sealing sheet 208 and or 210 with a water impermeable pressure sensitive or hot melt adhesive and making appropriate contact with the circuit substrate material such that the circuit components are sealed within and protected from coming in contact with external liquids.

Alternatively, the materials used for the sealing sheet, conductive adhesive, and substrate may be selected such that a waterproof seal may be formed by applying heat and pressure to the appropriate contact areas and then heat bond these materials such that a waterproof seal is formed.

Figure 6:
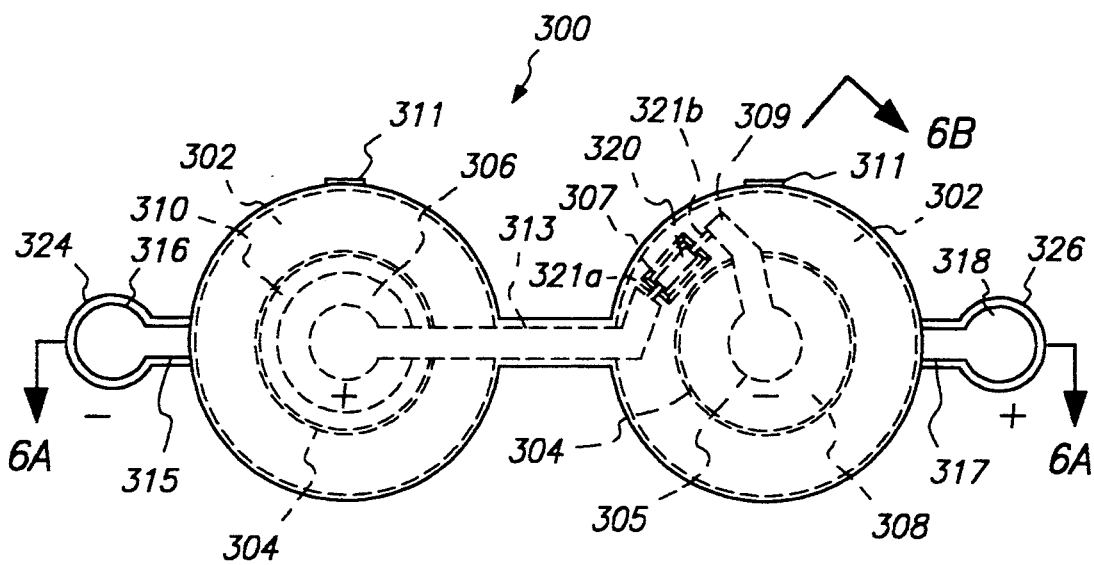
FIG. 6 is a plan view of an additional embodiment in accordance with the invention.
Figure 7:
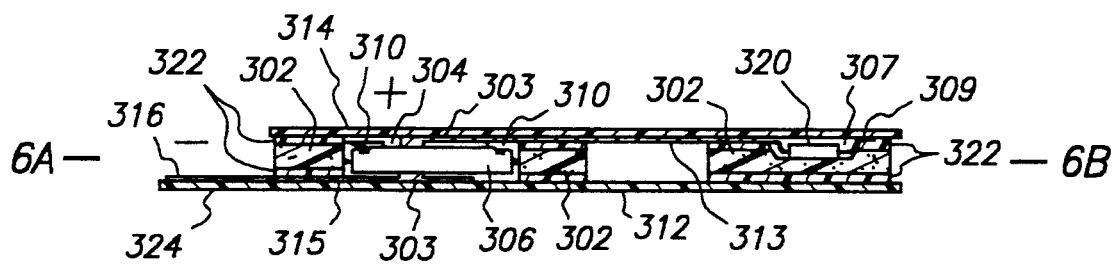
FIGS. 7 and 8 are cross sectional views of the apparatus of FIG. 6 taken along lines 6A–6B and 6A–6A, respectively.
Figure 8:
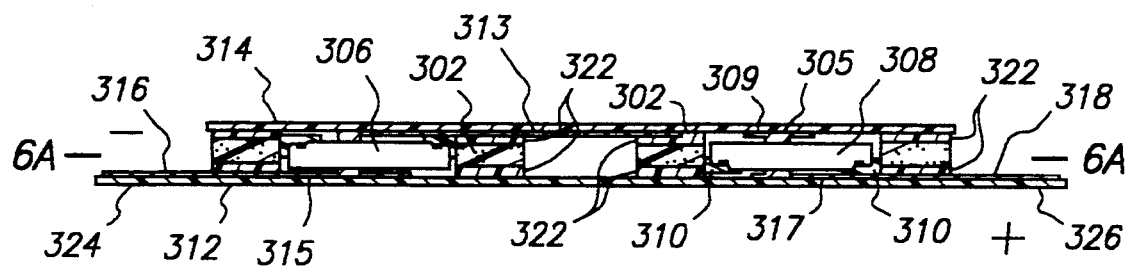

With reference to FIGS. 6, 7 and 8 an alternate embodiment of an electrical power network in accordance with the present invention is illustrated generally by the numeral 300. Electrically insulating and liquid impermeable foam spacers 302 made of a closed cell foam, for example MED6601 made by Avery Dennison, Chicago, Il., are provided with recessed pockets 304 and pocket 307. Pockets 304 receive batteries 306 and 308; pocket 307 receives electrical component 320 therein.

The component used in this embodiment is a current controlling diode 320 such as CRR0240 made by Siliconix, Santa Clara, Ca. Diode 320 controls the current from the batteries 306 and 308 for electrotransport delivery of a therapeutic drug or other agent from a liquid containing donor electrode assembly (not shown).

Alternate components may be used as previously described above with additional recessed pockets and conductive traces for appropriate connections.

Electrically insulating and liquid impermeable bottom substrate 312 and top substrate 314 provide a top and bottom seal for the batteries 306, 308 and component 320. The substrates 312 and 314 are thin polyester or polyurethane sheets about 0.1 mm thick. The substrates 312 and 314 carry electrically conductive top circuit traces 309, 313 and bottom traces 315 and 317 facing the foam spacers 302. Traces 309, 313, 315 and 317 are etched copper for connecting the batteries 306, 308 and component 320. Traces 309, 313, 315 and 317 may alternately be comprised of silk-screened silver ink.

Each battery 306 and 308 is provided with an insulating rim 310 to electrically isolate the conductive strips 309, 313 from shorting between the plus and minus terminals of the batteries where the strips 309, 313 cross the outer diameter of the battery case. Button cell batteries of this type are available from Panasonic, Secaucus, N.J.

Substrates 312 and 314 may be formed from separate pieces or alternately may be formed from one piece and folded at a suitable hinge line 311.

Substrates 312 and 314 are sealed to the spacers 302 around the perimeter of the top and bottom surfaces respectively. A peripheral seal 322 completely around the perimeter of spacers 302 is provided by an electrically insulating and liquid impermeable adhesive such as Silicone Medical Adhesive, made by Dow Corning Co., Midland, Mi. This adhesive also provides an electrically insulating and liquid tight seal between the respective substrates and the conductive traces 315 and 317 where they extend through the peripheral seal 322 of the spacers 302.

These extensions of the conductive traces 315 and 317 provide power network outputs 316 and 318 for connecting the power network 300 to a closely adjacent ionic liquid containing donor and counter donor electrode assemblies of an electrotransport drug delivery system as described above.

The first battery 306 negative terminal is connected to the power network output 316. The positive terminal of the first battery 306 connects to the top conductive trace 313. The trace 313 passes through the peripheral seal 322 of the first spacer 302 and enters through the peripheral seal 322 of the second spacer 302 to make electrical contact with one terminal 321a of the component 320. The other terminal 321b of the component 320 is connected to the top conductive trace 309 of the second spacer 302. The top trace 309 connects to the negative first terminal of the second battery 308. The positive terminal of the second battery 308 connects to the bottom trace 317. The bottom trace 317 passes through the bottom peripheral seal 322 of the second spacer 302 and forms the positive power network output 318 of the electrotransport power supply.

The substrate 312 is extended laterally to form supports 324 and 326. Support extensions 324 and 326 provide mechanical support for the power network outputs 316 and 318 outside of the spacers 302.

The power network outputs 316 and 318 are connected to appropriate donor and counter donor electrodes by a suitable conductive means such as silver loaded epoxy.

What is claimed is:

1. A sealed electrical power network for powering an electrotransport device for delivery of a beneficial agent though a body surface of a patient, the power network including one or more electrical components, two or more power network outputs, means for electrically connecting the electrical component to the power network outputs, and means for electrically connecting at least one of said power network outputs to an electrode holding a liquid, further comprising:
   a liquid-tight chamber sealed to surround and enclose the power network, the chamber providing liquid-tight passage for the power network outputs, whereby the power network is seal ed from contacting said liquid.

2. The power network of claim 1, wherein the liquid-tight chamber is comprised of a water impermeable film.

3. The power network of claim 2, wherein the water impermeable film is comprised of a heat sealable material.

4. The power network of claim 1, wherein said one or more electrical components includes an electrical power source.

5. The power network of claim 4, wherein said electrical power source comprises a battery.

6. The power network of claim 1, wherein said one or more electrical components includes an electrical component for controlling the electric current supplied to the power network outputs.

7. The power network of claim 6, wherein the electrical component for controlling the electrical current is selected from the group consisting of transistors, switches, diodes, resistors, timers, integrated circuits and combinations thereof.

8. The power network of claim 1, wherein said means for electrically connecting comprises an electrically conductive adhesive strip.

9. The power network of claim 1, wherein said liquid-tight chamber is comprised of a liquid impermeable substrate having a pocket formed therein, said one or more electrical components being positioned in said pocket.

10. The power network of claim 1, wherein said means for electrically connecting comprises an electrically conductive trace on said substrate.

11. The power network of claim 9, including a cover over said pocket, said cover being sealed to the substrate around said pocket.

12. The power network of claim 11, wherein said electrically connecting means comprises an electrically conductive trace on said cover.

13. An electrotransport device having the power network of claim 1.

14. The device of claim 1 or 13, wherein the electrode comprises a donor electrode holding the agent to be delivered.

15. The device of claim 1 or 13, wherein the electrode comprises a counter electrode holding an electrolyte.

16. A method of sealing, in a liquid-tight manner, a network for powering an electrotransport device for delivery of a beneficial agent through a body surface of a patient, the method comprising:
 placing the power network in a chamber formed at least in part of a liquid impermeable material, which power network includes one or more electrical components and means for electrically connecting said one or more electrical components to a pair of power network outputs, at least one of said outputs being for electrical connection to a closely adjacent electrode holding a liquid which contains the beneficial agent to be delivered;
 positioning the outputs so the outputs extend from inside the chamber to outside the chamber; and
 sealing the power network within said chamber in a liquid-tight manner so that the outputs are accessible for electrical connection outside the chamber, whereby the power network is sealed from contacting the liquid.

17. The method of claim 16, further comprising electrically connecting one of said pair of outputs to a closely adjacent electrode holding a liquid and the beneficial agent to be delivered.

18. The method of claim 17, further comprising electrically connecting a second electrode holding a liquid containing an electrolyte to the other of said pair of outputs.

19. The method of claim 16, wherein the chamber is formed at least in part of a heat sealable material and further comprising sealing said chamber by heat sealing said material.

20. The method of claim 16, including forming said chamber by forming a pocket in a liquid impermeable substrate, placing a cover over said pocket and sealing said cover to said substrate around said pocket.

21. The method of claim 20, wherein the cover is adhesively sealed to the substrate.

* * * * *